(12) United States Patent
Biedermann et al.

(10) Patent No.: US 8,157,843 B2
(45) Date of Patent: Apr. 17, 2012

(54) FLEXIBLE STABILIZATION DEVICE FOR DYNAMIC STABILIZATION OF BONES OR VERTEBRAE

(75) Inventors: Lutz Biedermann, VS-Villingen (DE); Wilfried Matthis, Weisweil (DE); Helmar Rapp, Deißlingen (DE)

(73) Assignee: Biedermann Motech GmbH & Co. KG, Villingen-Schwenningen (DE)

( * ) Notice: Subject to any disclaimer, the term of this patent is extended or adjusted under 35 U.S.C. 154(b) by 519 days.

(21) Appl. No.: 11/642,566

(22) Filed: Dec. 19, 2006

(65) Prior Publication Data

US 2007/0233085 A1    Oct. 4, 2007

Related U.S. Application Data

(60) Provisional application No. 60/753,620, filed on Dec. 23, 2005.

(30) Foreign Application Priority Data

Dec. 23, 2005    (EP) ..................................... 05028283

(51) Int. Cl.
A61B 17/70    (2006.01)
(52) U.S. Cl. ........................................ 606/255; 606/257
(58) Field of Classification Search ................. 606/246, 606/254–257, 259–263, 264, 277; 623/17.11, 623/17.13, 17.15, 17.16
See application file for complete search history.

(56) References Cited

U.S. PATENT DOCUMENTS

| 5,042,982 | A |   | 8/1991  | Harms et al. |
|-----------|---|---|---------|--------------|
| 5,330,473 | A | * | 7/1994  | Howland ...................... 606/250 |
| 5,480,401 | A | * | 1/1996  | Navas ........................... 606/256 |
| 5,540,688 | A |   | 7/1996  | Navas |
| 5,545,164 | A | * | 8/1996  | Howland ...................... 606/250 |
| 5,653,708 | A | * | 8/1997  | Howland ...................... 606/264 |
| 6,290,700 | B1| * | 9/2001  | Schmotzer .................... 606/263 |
| 7,611,518 | B2|   | 11/2009 | Walder et al. |
| 2002/0035366 | A1 |  | 3/2002 | Walder et al. |
| 2002/0173791 | A1 | * | 11/2002 | Howland ...................... 606/61 |
| 2003/0083657 | A1 |  | 5/2003 | Drewry et al. |
| 2003/0220642 | A1 |  | 11/2003 | Freudiger |
| 2003/0220643 | A1 |  | 11/2003 | Ferree |
| 2004/0049190 | A1 | * | 3/2004 | Biedermann et al. ........... 606/61 |

(Continued)

FOREIGN PATENT DOCUMENTS

EP          0516567 B1     12/1992

(Continued)

OTHER PUBLICATIONS

European Search Report for European Application No. 05028283.9-2318 dated Apr. 25, 2006 and mailed May 3, 2006, 5 pp.

(Continued)

*Primary Examiner* — Eduardo C Robert
*Assistant Examiner* — Jerry Cumberledge
(74) *Attorney, Agent, or Firm* — Christie, Parker & Hale, LLP (57) ABSTRACT

A flexible stabilization device for dynamic stabilization of bones or vertebrae is provided comprising a rod construct including a rod made of an elastomeric material the rod having a first connection section, a second connection section and a third section therebetween, the first and second connection sections being connectable with a bone anchoring device, respectively, and a sleeve provided on at least a portion of the third section of the rod such that at least the first and second connection sections are exposed.

13 Claims, 9 Drawing Sheets

U.S. PATENT DOCUMENTS

| | | | |
|---|---|---|---|
| 2004/0236327 A1* | 11/2004 | Paul et al. .................. 606/61 | |
| 2005/0056979 A1 | 3/2005 | Studer et al. | |
| 2005/0065514 A1 | 3/2005 | Studer | |
| 2007/0093821 A1 | 4/2007 | Freudiger | |

FOREIGN PATENT DOCUMENTS

| | | |
|---|---|---|
| EP | 0669109 B1 | 8/1995 |
| EP | 0669109 B1 | 8/1995 |
| EP | 1188416 A1 | 3/2002 |
| EP | 1364622 A2 | 11/2003 |
| JP | 02-500091 A | 1/1990 |
| JP | 07-255741 A | 10/1995 |
| JP | 2002-125980 A | 8/2002 |
| WO | WO 2004/105577 A2 | 12/2004 |

OTHER PUBLICATIONS

Search of the Austrian Patent Office by Serv.ip, "Ihr Partner für Forschung and Innovation Express-Recherche zum Stand der Technik," dated Feb. 13, 2006, 8 pp.

Office action from Japanese Counterpart Application (JP Application No. 336131/2006) dated Aug. 23, 2011, 3 pages and English Translation thereof (4 pages).

Office action dated Apr. 9, 2010 for U.S. Appl. No. 11/520,286 (12 pages).

* cited by examiner

FLEXIBLE STABILIZATION DEVICE FOR DYNAMIC STABILIZATION OF BONES OR VERTEBRAE

CROSS-REFERENCE TO RELATED APPLICATION(S)

The present disclosure claims the benefit of U.S. Provisional Patent Application Ser. No. 60/753,620, filed Dec. 23, 2005, and claims priority from European Patent Application EP05028283, filed Dec. 23, 2005, the entire disclosures of which are incorporated herein by reference.

BACKGROUND

The present disclosure relates to a flexible stabilization device for the dynamic stabilization of bones or vertebrae.

A flexible stabilization device for stabilizing adjacent vertebrae is known from EP 0 669 109 B1. In this stabilization device monoaxial bone screws placed in adjacent vertebrae are connected by an elastic strap. The strap is fastened to the bone screws in a pre-stressed manner. A support body which is resistant to compression surrounds the strap between the bone screws to transmit compressive forces. The support body, the heads of the bone screws and the elastic strap form a kind of joint allowing a limited motion of the vertebrae.

US 2003/0220643 A1 discloses a device for connecting adjacent vertebral bodies in which monoaxial pedicle screws are interconnected by a spring. The spring allows spinal flexion and a limited degree of lateral bending and axial rotation while preventing spinal extension without the need of a transverse member. A sleeve is placed over the spring. Impingement between the sleeve and the pedicle screws assists the spring in preventing spinal extension. The length of the spring is predetermined. An adaptation in length by the surgeon is not possible.

WO 2004/105577 A2 discloses a spine stabilization system with one or more flexible elements having an opening or slit in form of a helical pattern. Adjustments of the system with regard to its flexible characteristics are not possible during surgery.

A bone anchoring device comprising a monoaxial bone screw and a flexible rod which is made of an elastic material is known from EP 1 364 622 A2. The elastic characteristics of the bone anchoring device are determined by material and the shape of the rod which cannot be modified by the surgeon. Furthermore, the use of monoaxial bone screws limits the possibility of adjustment of the position of the shaft relative to the rod.

Based on the above, there is a need for a flexible stabilization device for dynamic stabilization of bones or vertebrae which allows modification of the elastic characteristics of the device and at the same time the adaptation of the length of the rod construct during the surgical operation.

SUMMARY OF THE INVENTION

A flexible rod assembly including an inner rod and outer rod or sleeve made of an elastomeric material allows an adjustment of the elastic characteristics of the stabilization device to a large extent. By means of selection of a rod and a sleeve with appropriate elastic properties which can be different from each other an adaptation of the elastic properties of the rod construct to the motion of a specific spinal segment is possible. In particular, flexion and compression of the spine can be controlled by means of the elastic properties of the inner rod, whereas extension of the spine can be controlled by selection of an appropriate sleeve. The separation of the damping with regards to flexion/compression and extension movements results in a harmonic behaviour of the vertebral segments under motion control of the construct. As a consequence thereof loosening of the bone screws can be prevented. Additionally, adjustment of the length of the inner rod and of the sleeve is possible. Hence, a modular system is provided which is allows adaptation at the time of surgery. In combination with polyaxial screws the possibilities of adjustment are further increased.

Further features and advantages of the disclosure will become apparent and will be best understood by reference to the following detailed description of embodiments taken in conjunction with the accompanying drawings.

BRIEF DESCRIPTION OF THE DRAWINGS

FIG. 2 shows an exploded view of a stabilization device comprising the rod construct of FIG. 1a.

FIG. 8a schematically shows the rod construct in a state of flexion according to FIG. 6a.

DETAILED DESCRIPTION OF THE INVENTION

Figure 1A:
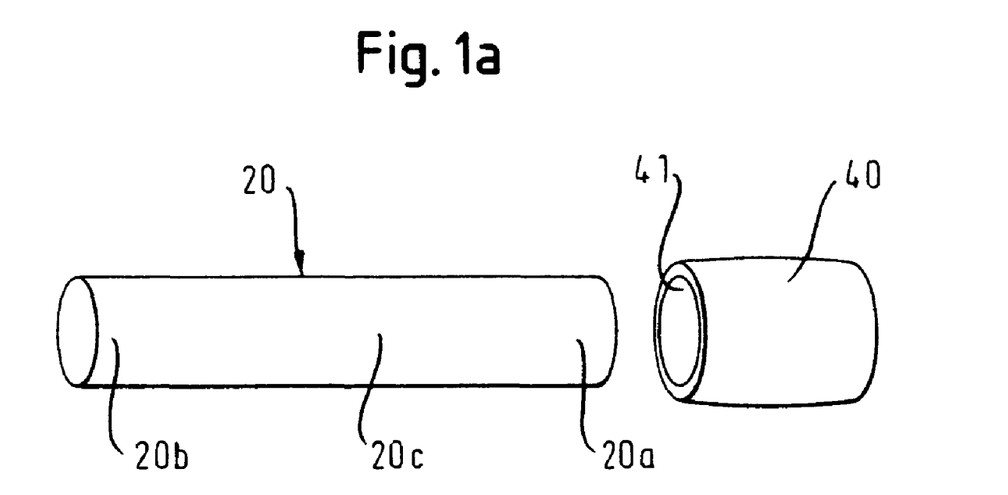
FIG. 1a shows a perspective exploded view of a rod construct according to an embodiment of the disclosure.
Figure 1B:
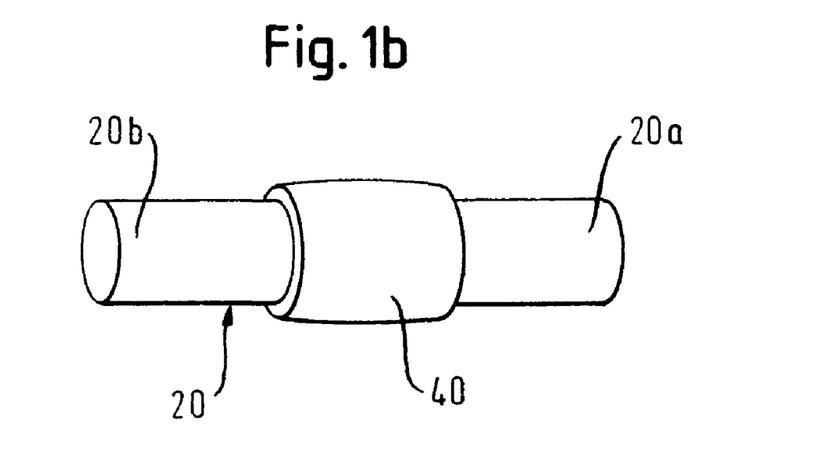
FIG. 1b shows the rod construct of FIG. 1a in an assembled state.

As shown in FIGS. 1a and 1b, the flexible stabilization device includes a rod assembly including rod 20 made of an elastomeric material and a sleeve 40 which is also made of an elastomer material. In the embodiment shown, the rod 20 has a cylindrical shape with a smooth surface. Due to the elastomer material, the rod is partially or fully flexible. For example, the rod 20 can be made of a biocompatible plastic material such as a polymer on the basis of polyurethane, polysilicone or PEEK. A particularly suitable material is Polycarbonate Urethane. The material of the rod includes well-defined elastic properties and the rod shows bending elasticity, compressive elasticity and tensile elasticity.

The elastomeric material of the sleeve 40 can also be a biocompatible plastic material such as a polymer on the basis of polyurethane, polysilicone or PEEK which includes elastic properties which can be selected independently of the elastic properties of the rod 20. Also for the sleeve 40, Polycarbonate Urethane is particularly suitable. The sleeve 40 has a tube-like shape including a channel 41 the diameter of which is slightly larger than the outer diameter of the rod 20 so that the rod 20 can be inserted into the channel 41 as shown in FIG. 1b. The length of the sleeve 40 is selected to be smaller than the length of the rod 20 such that a first connection section 20a and a second connection section 20b of the rod 20 protrude from the channel 41 in the assembled state as shown in FIG. 1b. A section 20c between the first connection section 20a and the second connection section 20b of the rod 20 is accommodated in the channel 41 of the sleeve 40. Preferably the length of the sleeve 40 corresponds approximately to the distance between the receiving parts of the bone anchoring devices, or can be slightly larger.

Figure 2:
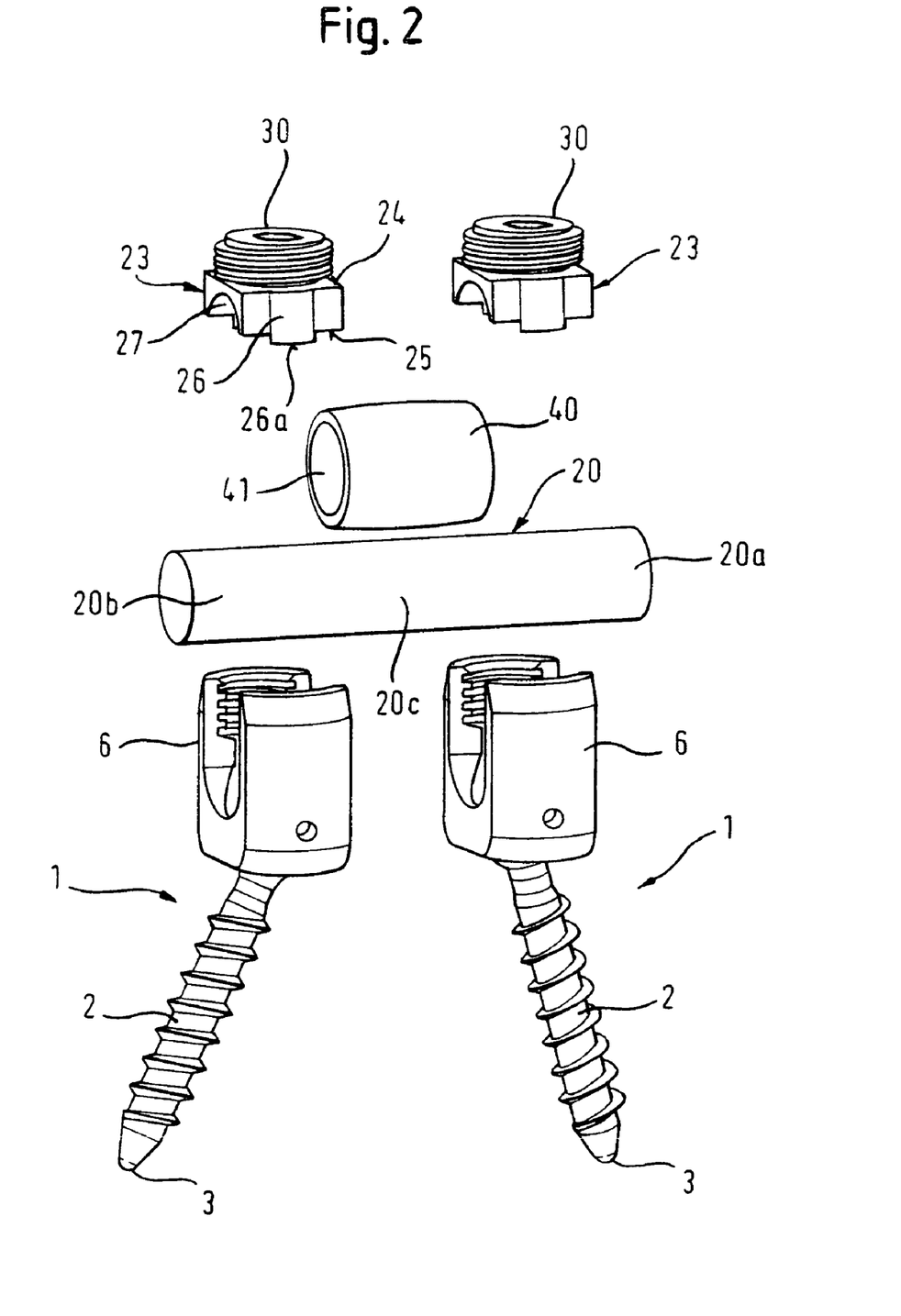
Figure 3:
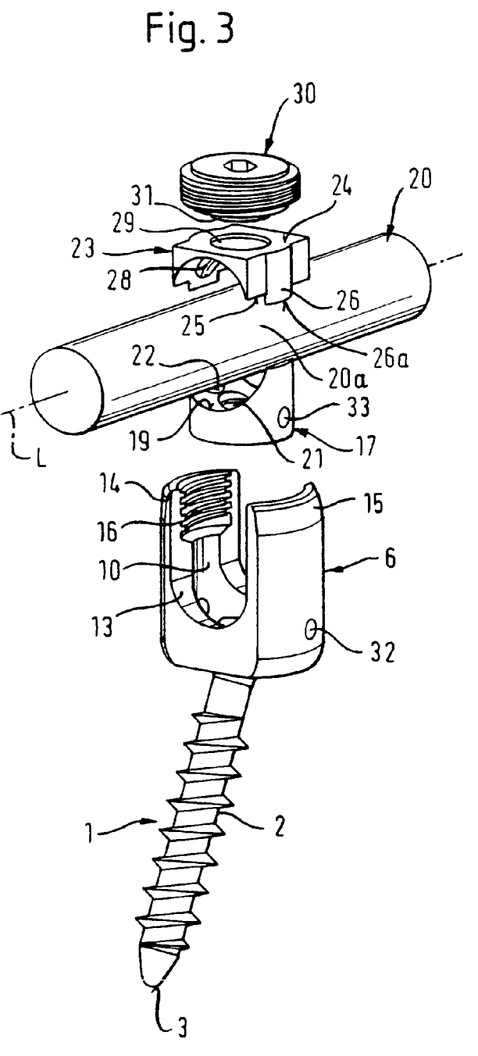
FIG. 3 schematically shows in an exploded view the accommodation of the rod of FIG. 1a in the receiving part of a polyaxial bone screw.
Figure 4:
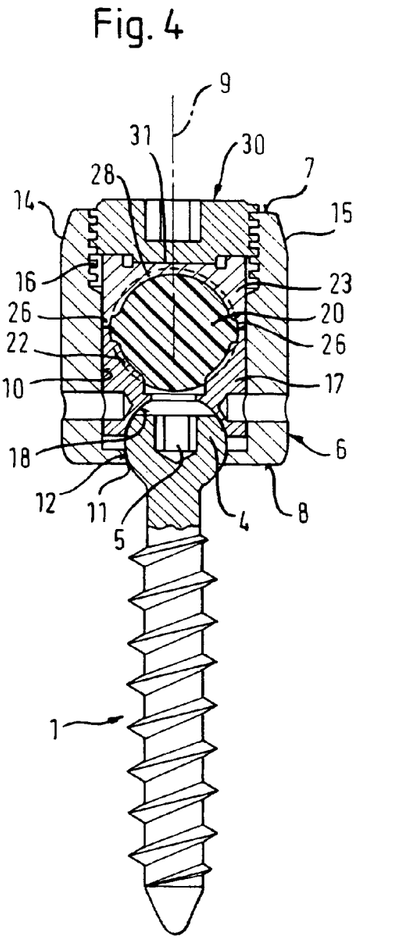
FIG. 4 shows a sectional view of the assembled parts of FIG. 3.

With reference to FIGS. 2 to 4 the connection of the rod 20 with the receiving part 6 of a bone anchoring element 1 is explained. Although the sleeve 40 is omitted in the illustration of FIG. 3, for the purpose of describing the connection of the rod 20 with the receiving part 6, the sleeve 40 is placed on the rod 20 before the latter is secured to the respective receiving parts 6 of the bone anchoring elements 1.

The bone anchoring element 1 in this embodiment is a polyaxial bone screw having a shank 2 with a bone thread, a tip 3 at one end and a spherical head 4 at the opposite end. A recess 5 for engagement with a screwing-in tool is provided at the side of the head 4 which is opposite to the shank. The receiving part 6 has a first end 7 and a second end 8 opposite to the first end and a longitudinal axis 9 intersecting the plane of the first end and the second end. Coaxially with the longitudinal axis 9 a bore 10 is provided which extends from the first end 7 to a predetermined distance from the second end 8. At the second end 8 an opening 11 is provided the diameter of which is smaller than the diameter of the bore 10. A spherical or otherwise tapering section 12 is provided adjacent of the opening 11 which forms a seat for the spherical head 4.

The receiving part 6 further has a U-shaped recess 13 which starts at the first end 7 and extends in the direction of the second end 8 to a predetermined distance from said second end 8. By means of the U-shaped recess 13 two free legs 14, 15 are formed extending towards the first end 7. Adjacent to the first end 7 the receiving part 6 comprises an internal thread 16 on said legs 14, 15.

As can be seen in FIG. 3, a first pressure element 17 is provided which has a cylindrical construction with an outer diameter which is only slightly smaller than the inner diameter of the bore 10 to allow the first pressure element 17 to be introduced into the bore 10 of the receiving part 6 and to be moved in the axial direction. On its lower side facing towards the second end 8, the pressure element 17 includes a spherical recess 18 the radius of which corresponds to the radius of the spherical head 4 of the bone screw. On the opposite side, the first pressure element 17 has a cylindrical recess 19 which extends transversely to the longitudinal axis 9. The lateral diameter of this recess is selected such that the connection section 20a or 20b with a circular cross section, respectively, of the rod 20 which is to be received in the receiving part 6 can be inserted into the recess 19 and guided laterally therein. The depth of the cylindrical recess 19 is selected such that in an assembled state when the connection section 20a or 20b of the rod 20 is inserted and pressed against the bottom of the U-shaped recess 13, the first pressure element 17 exerts a pressure on the head 5. Further the depth is preferably about half of the diameter of the connection section 20a or 20b of the rod 20. As can be seen in FIG. 3, the first pressure element 17 has a coaxial bore 21 for guiding a screwing-in tool therethrough.

As shown in FIGS. 3 and 4, the bone anchoring element 1 further comprises a second pressure element 23 with a first end 24 and a second end 25. The width of the second pressure element 23 is such that the second pressure element 23 can be inserted into the U-shaped recess 13 of the receiving part 6. On opposite sides of the second pressure element 23 two cylindrical projections 26 are provided which fit into the space limited by the internal thread 16 to slide along the internal thread 16 when the second pressure element 23 is inserted.

As can be seen in FIG. 2, the second pressure element 23 further includes a cylindrical recess 27 extending from the second end 25 in the direction towards the first end 24 the cylinder axis of which is perpendicular to that of the cylindrical projections 26. On the side of the second end 25, the cylindrical projections 26 include lower edges 26a. The diameter of the cylindrical recess 27 corresponds to the diameter of the connection section 20a or 20b of the rod 20 and its depth to half or less than half of the diameter of the connection section 20a or 20b.

The bone anchoring element 1 further includes an inner screw 30 which can be screwed-in between the legs 14, 15. The internal thread 16 and the cooperating thread of the inner screw 30 can have any known thread shape. Using a flat thread or a negative angle thread can prevent splaying of the legs 14, 15.

The receiving part 6 and the first pressure element 17 can have corresponding crimp bores 32, 33 on opposite sides by means of which the screw 1, the receiving part 6 and the first pressure element 17 can be loosely pre-assembled. As shown in FIG. 3 and 4 the first pressure element 17 and the second pressure element 23 can have projections 22, 28, respectively, which can contribute to the fixation of the elastic rod 20.

The other parts of the flexible stabilization device except the rod 20 and the sleeve 40 can be made of the commonly used biocompatible materials, such as stainless steel or titanium or any other material suitable for a bone screw.

In use, at least two bone anchoring devices are anchored into the bone. Next, the rod 20 and the sleeve 40 are selected and combined to achieve the desired elastic properties of the flexible stabilization device. If, for example, more than two vertebrae are to be connected, different sleeves 40 having different elastic properties can be selected and provided between different vertebrae. In this way, the elastic properties of the stabilization device can be adapted at the time of surgery. Preferably, the sleeve 40 is selected to have a length corresponding to the distance of the two receiving parts when the pedicle screws are screwed into adjacent vertebrae. Since the rod 20 and the sleeve 40 are made of elastomeric material, shortening during surgery is possible. Then, rod 20 with the sleeve 40 or, if more that one motion segment shall be stabilized via a single rod 20, with a plurality of sleeves 40 is inserted into the receiving parts 6 of the bone anchoring elements. Preferably, in the balanced position of the two adjacent vertebrae, the sleeve 40 is in contact with the receiving parts 6.

Thereafter, the second pressure element 23 is inserted in the receiving part 6 and the inner screw 30 is screwed-in between the legs 14, 15. After adjusting the angular position of the bone screw, the inner screw 30 is tightened. By the pressure exerted by the inner screw 30 onto the second pressure element 23, the rod 20 is clamped between the first and the second pressure element 17, 23 and simultaneously the head 4 of the bone screw is locked in its angular position.

Figure 5:
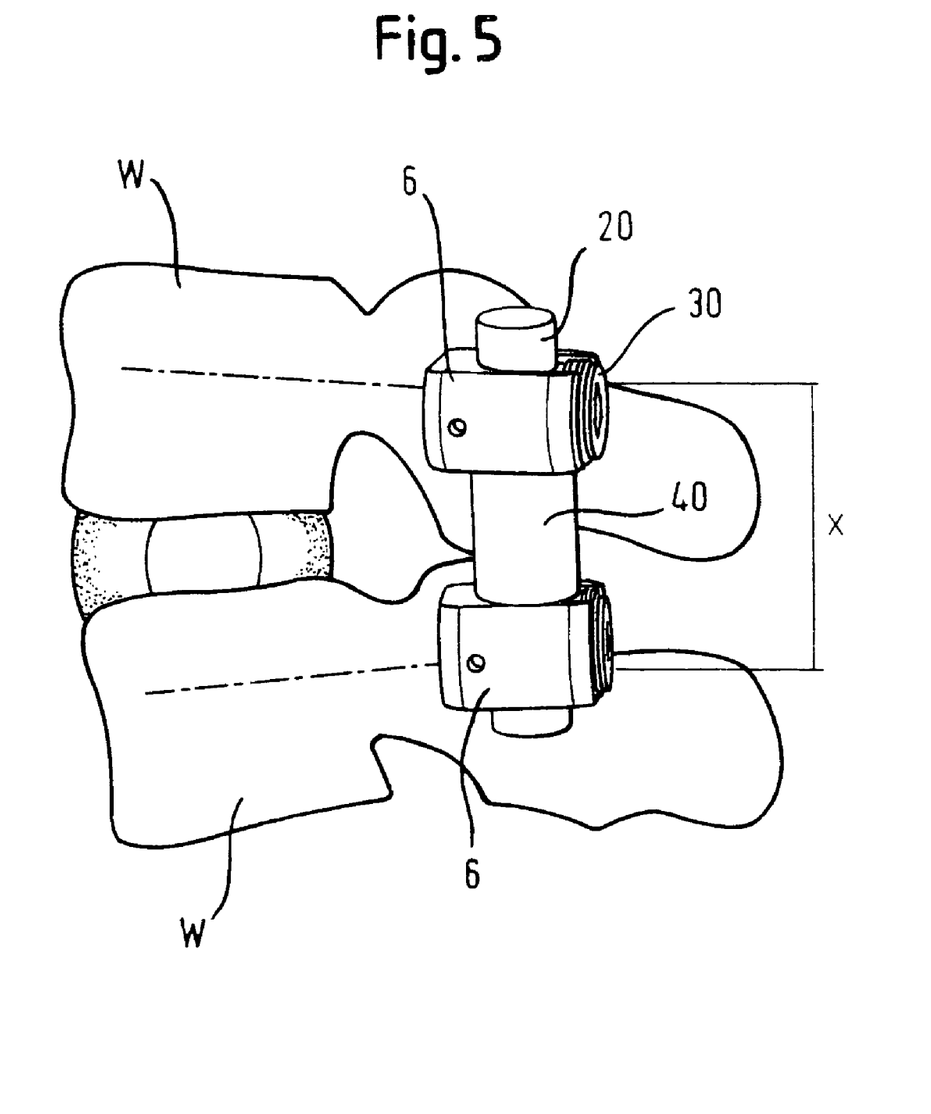
FIG. 5 schematically shows the assembled stabilization device of FIG. 2 applied to adjacent vertebrae of the spinal column.

Next, with reference to FIGS. 5 to 8b the elastic properties of the flexible stabilization device are described. In FIG. 5 the assembled stabilization device is shown with the rod 20 and the sleeve 40 arranged to connect two polyaxial pedicle screws which are placed in adjacent vertebrae W forming a motion segment. The positions of the shanks of the pedicle screws are indicated by dash-dotted lines. As can be seen in FIG. 5, the receiving parts 6 of the bone anchoring elements 1 have a distance x in the balanced position in which the rod 20 and the sleeve 40 are in an unstressed state.

Figure 6A:
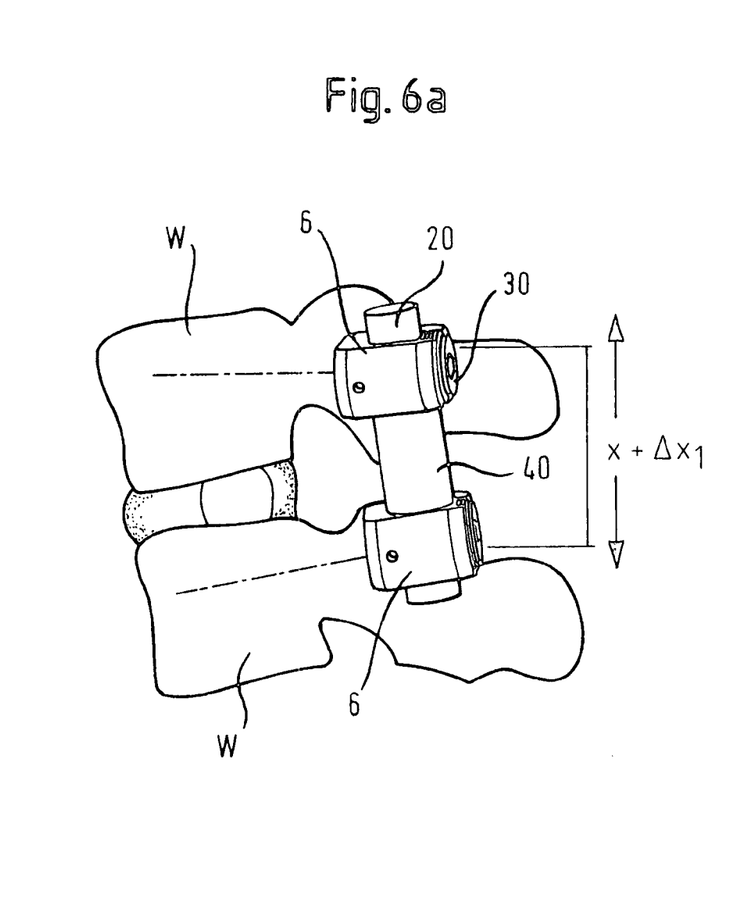
FIG. 6a schematically shows the stabilization device of FIG. 5 with the spinal column in flexion.

FIG. 6a shows the stabilization device when flexion takes place. During flexion, tensile stress is applied to the rod 20 resulting in an elongation of the rod 20. The distance between the bone anchoring elements is increased to $x+\Delta X_1$. The increase $\Delta X_1$ in the distance is limited by the restoring force produced by the rod 20 due to its elastic properties. The increase in the distance can be, for example, in the range of approximately 1.5 mm. Hence, flexion/compression is controlled mainly by the inner rod 20.

Figure 6B:
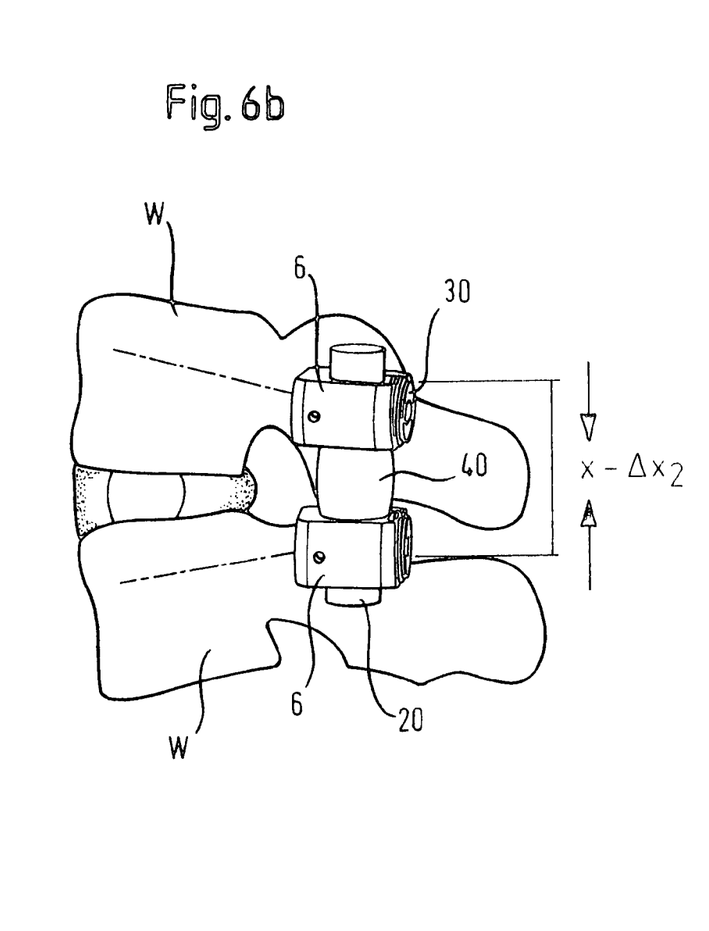
FIG. 6b schematically shows the stabilization device of FIG. 5 with the spinal column in extension.

FIG. 6b shows the stabilization device when extension takes place. During extension, a compressive force is applied to the rod 20 and the sleeve 40 by the receiving parts 6 of the bone anchoring elements 1. The elasticity of the rod 20 and the sleeve 40 allows the distance between the receiving parts 6 to decrease to a distance $x-\Delta x_2$. Due to the elastic properties of the rod 20 and the sleeve 40, a restoring force acts on the receiving parts 6 which limits the decrease of the distance. The distance can, for example, decrease by approximately 0.5 mm. Hence, extension is controlled by the compressibility of the inner rod 20 and is limited by the sleeve.

In an alternative manner of application, the sleeve 40 can be pre-compressed in the balanced state and/or the rod 20 can be pre-stressed in the balanced state.

Figure 7:
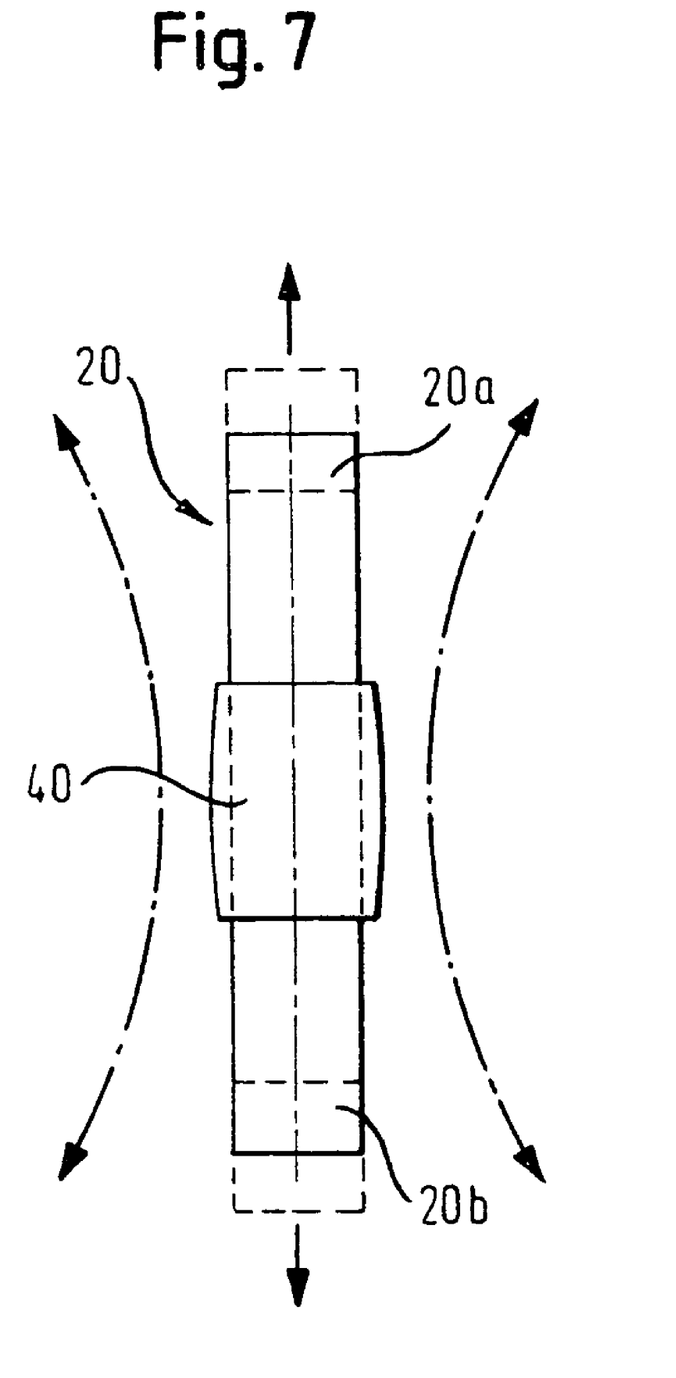
FIG. 7 schematically illustrates the directions of displacement of the rod construct of FIG. 1b.
Figure 8A:
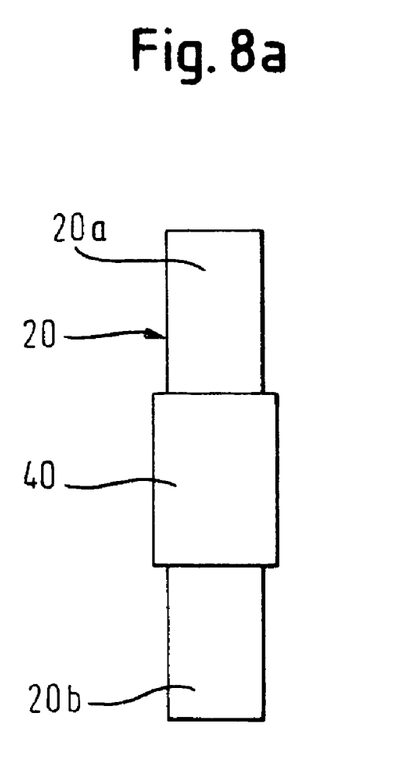
Figure 8B:
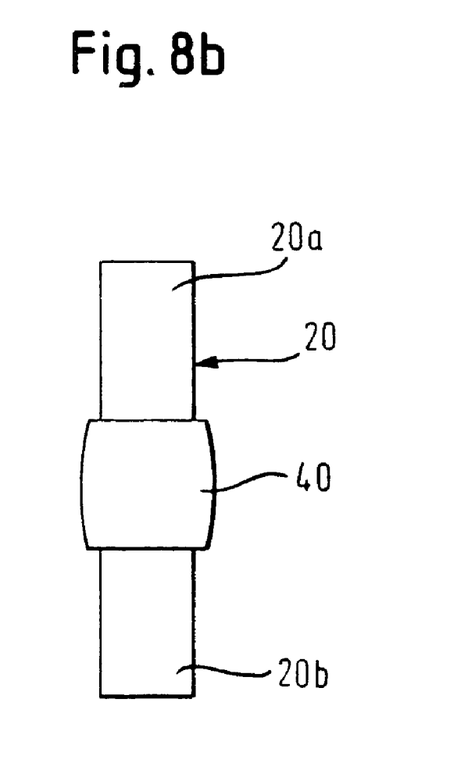
FIG. 8b schematically shows the rod construct in a state of extension according to FIG. 6b.

FIG. 7 illustrates the possible deformations which the rod 20 and the sleeve 40 can undergo. FIGS. 8a and 8b show the deformation of the rod 20 and the sleeve 40 in flexion (FIG. 8a) and in extension (FIG. 8b).

Figure 9A:
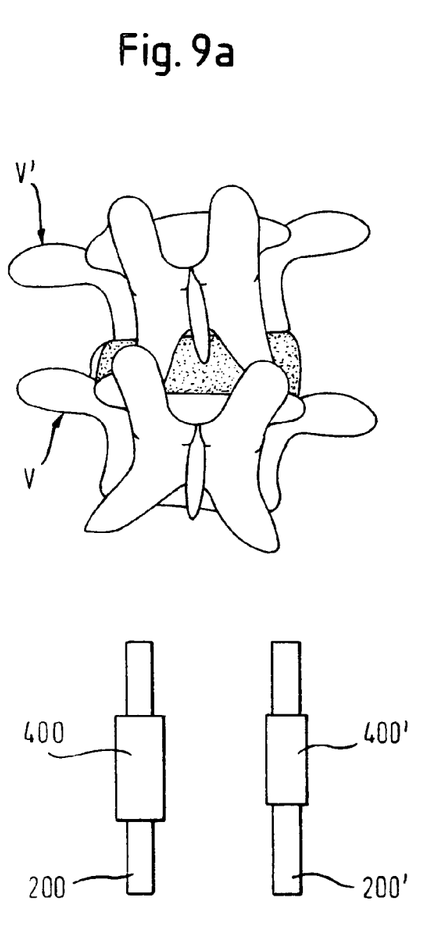
FIGS. 9a and 9b show a further example of application of the stabilization device in a top view.
Figure 9B:
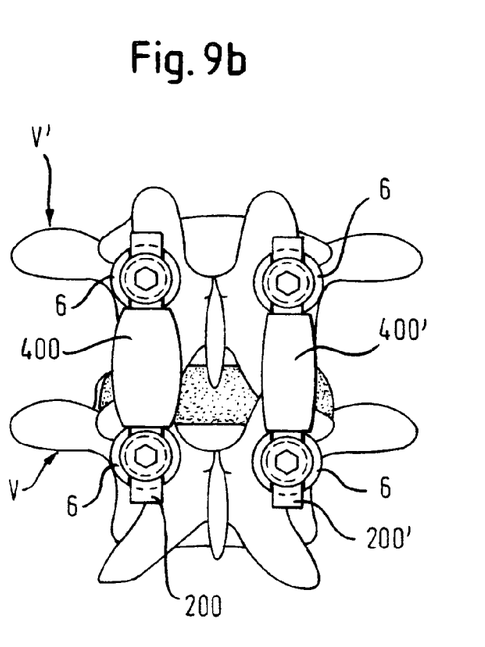

FIGS. 9a and 9b show an example of application of the stabilization device. FIG. 9a shows two adjacent vertebrae V, V' which are medio-laterally inclined with respect to each other in the case of the presence of scoliosis. To dynamically stabilize and correct such a motion, segment rods 200, 200' with different sleeves 400, 400' can be used on the left side and on the right side. The sleeve 400 used on the left side rod 200 has a length which is greater than the length of sleeve 400' used on the right side rod 200'. In this manner, it is possible to eliminate the inclination of two vertebrae on the left side. In addition, the outer diameter of the sleeve 400 can be different from that of the sleeve 400' in order to have a different motion control with respect to the left side and the right side.

Further modifications of the above described embodiments are possible. In the embodiment described before, the sleeve 40 has the shape of a hollow cylinder; however, different shapes of the sleeve are possible. For example, a barrel-shape is possible. The length of the sleeve can differ from the embodiment shown. The rod 20 may also have a rectangular, square, oval or triangular cross-section or any other appropriate shape of the cross-section. In this case, the shape of the sleeve 40 is appropriately adapted. In particular, it is possible to form the rod 20 and/or the sleeve 40 with the shape varying in the longitudinal direction. The rod 20 and the sleeve 40 can be formed to be highly flexible or hardly flexible.

Figure 10:
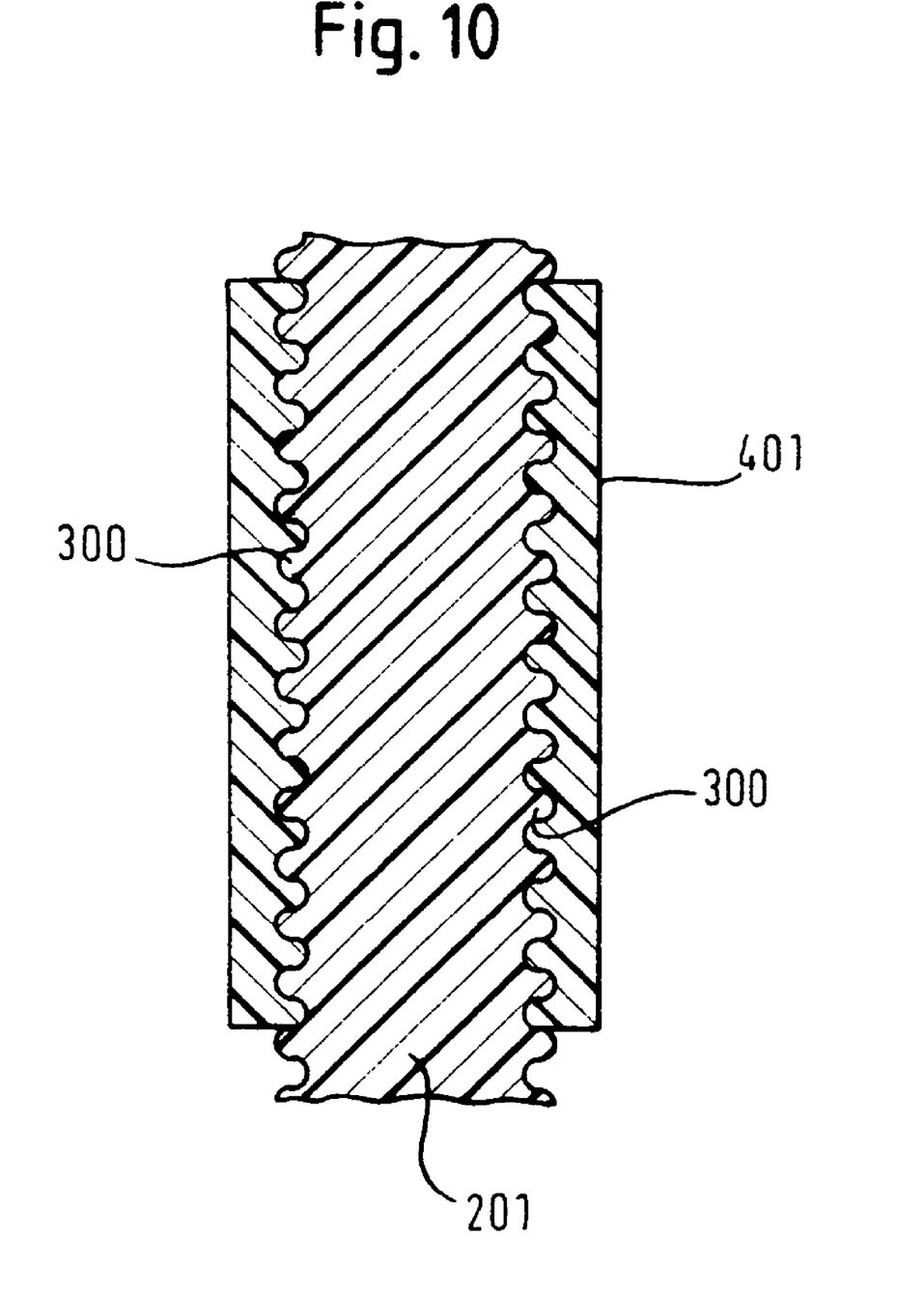
FIG. 10 shows modification of the rod construct in section.

The surface of the rod 20 and/or the sleeve 40 can be textured or structured. FIG. 10 shows an example of an inner rod 201 having a corrugated surface, with corrugations 300 provided in the circumferential direction. The inner wall of the sleeve 401 has corresponding corrugations cooperating with that of the rod. This prevents or reduces a displacement of the sleeve relative to the rod.

In the example of the bone anchoring element described above, the connection of the shanks 2 of the bone anchoring elements 1 to the respective receiving parts 6 is polyaxial. However, it is also possible to provide a monoaxial connection.

For the inner screw 30, all known modifications can be used. This includes also the use of an outer ring or nut.

In the embodiments described, the bone anchoring element 1 is introduced from the top into the receiving part 6. However, the bone anchoring element 1 can also be introduced from the bottom of the receiving part 6 if the receiving part 6 is constructed to allow this.

The head of the bone anchoring element and the shaft can be constructed as separate parts which can be connected.

The present disclosure is not limited to screws as bone anchoring elements but can be realized with bone hooks or any other bone anchoring element.

What is claimed is:

1. A flexible stabilization device for dynamic stabilization of bones or vertebrae comprising:
a rod assembly comprising:
a rod made of an elastomeric material having bending elasticity, compressive elasticity, and tensile elasticity and structured such that its length is adjustable, the rod having a first connection section, a second connection section and a third section therebetween and extending along a rod axis, and
a sleeve configured to be provided on at least a portion of the third section of the rod, a length of the sleeve being smaller than a length of the rod, such that at least the first and second connection sections are exposed;
a first bone anchoring device and a second bone anchoring device, each of the bone anchoring devices comprising:
a shank portion configured to be anchored in a bone or in a vertebra;
a head portion having a recess configured to receive the first connection section or the second connection section of the rod; and
a securing element configured to secure the first connection section or the second connection section in the recess;
wherein the first bone anchoring device and the second bone anchoring device are moveable from a first position being a first distance apart from each other along the rod axis to a second position being a second distance apart along the rod axis less than the first distance;
wherein the rod has a compressive elasticity sufficient to transmit a force along the rod axis to bias the first anchoring device and the second anchoring device toward the first position from the second position, when the rod is straight and compressed between the first anchoring device and the second anchoring device.

2. A flexible stabilization device according to claim 1, wherein the sleeve is made of an elastomeric material.

3. A flexible stabilization device according to claim 2, wherein the elastic properties of the rod and the sleeve are different.

4. A flexible stabilization device according to claim 2, wherein the elastomeric material of the rod or the sleeve is a biocompatible plastic.

5. A flexible stabilization device according to claim 4 wherein the biocompatible plastic material comprises polyurethane or polysilicone.

6. A flexible stabilization device according to claim 1, wherein the inner wall of the sleeve is in contact with the surface of the rod.

7. A flexible stabilization device according to claim 1, wherein at least one of the bone anchoring devices is constructed so as to allow a polyaxial connection between a shank of the bone anchoring device and the rod.

8. A flexible stabilization device according to claim 1, wherein the sleeve is configured as a solid annular sleeve surrounding an entire exposed surface of the third section of the rod.

9. A flexible stabilization device for dynamic stabilization of bones or vertebrae comprising:
- a rod assembly for a flexible stabilization device, the rod assembly comprising:
  - a rod made of an elastomeric material having bending elasticity, compressive elasticity, and tensile elasticity, the rod having a first connection section, a second connection section and a third section therebetween and extending along a rod axis, at least an outer surface of the third section comprising a shape that is varied along the rod axis due to at least one of a plurality of projections and a plurality of grooves that extend transversely to the rod axis; and
  - a sleeve configured to be provided on at least a portion of the third section of the rod such that at least the first and second connection sections are exposed, an inner surface of the sleeve comprising at least the other of a plurality of projections and a plurality of grooves;
- a first bone anchoring device and a second bone anchoring device, each of the bone anchoring devices comprising:
  - a shank portion configured to be anchored in a bone or in a vertebra;
  - a head portion having a recess configured to receive one of the first connection section and the second connection section of the rod; and
  - a securing element configured to secure the first connection section or the second connection section in the recess;
- wherein the projections correspond to the grooves and are configured to engage each other to provide a form-fit connection;
- wherein each of the plurality of projections and each of the plurality of grooves extend around the rod.

10. A rod assembly according to claim 9, wherein the sleeve is made of an elastomeric material.

11. A rod assembly according to claim 10, wherein the elastic properties of the rod and the sleeve are different.

12. A rod assembly according to claim 10, wherein the elastomeric material of rod or the sleeve is a biocompatible plastic.

13. A rod assembly accordingly to claim 12 wherein the biocompatible plastic material comprises polyurethane or polysilicone.

* * * * *